United States Patent
Field et al.

(10) Patent No.: US 10,813,716 B2
(45) Date of Patent: *Oct. 27, 2020

(54) SELF-CONTAINED, SELF-PIERCING, SIDE-EXPELLING MARKING APPARATUS

(71) Applicants: Bard Peripheral Vascular, Inc., Tempe, AZ (US); BARD SHANNON LIMITED, Nieuwegein (NL)

(72) Inventors: Steven E. Field, Grand Rapids, MI (US); Ryan L. Goosen, Caledonia, MI (US); Brian R. Mulder, Rockford, MI (US); Richard M. Chesbrough, Bloomfield Hills, MI (US)

(73) Assignees: Bard Peripheral Vascular, Inc., Franklin Lakes, NJ (US); Bard Shannon Limited, Nieuwegein (NL)

( * ) Notice: Subject to any disclaimer, the term of this patent is extended or adjusted under 35 U.S.C. 154(b) by 411 days.

This patent is subject to a terminal disclaimer.

(21) Appl. No.: 15/853,052

(22) Filed: Dec. 22, 2017

(65) Prior Publication Data

US 2018/0200019 A1 Jul. 19, 2018

Related U.S. Application Data

(60) Continuation of application No. 15/381,717, filed on Dec. 16, 2016, now Pat. No. 9,848,956, which is a
(Continued)

(51) Int. Cl.
*A61B 5/00* (2006.01)
*A61B 90/00* (2016.01)
*A61B 5/06* (2006.01)

(52) U.S. Cl.
CPC .............. *A61B 90/39* (2016.02); *A61B 5/064* (2013.01); *A61B 2090/3908* (2016.02); *A61B 2090/3987* (2016.02)

(58) Field of Classification Search
CPC ............ A61B 90/39; A61B 2090/3908; A61B 2090/3987; A61B 5/062; A61B 5/064; A61B 5/055; A61B 10/02; A61B 10/0233
See application file for complete search history.

(56) References Cited

U.S. PATENT DOCUMENTS 2,899,362 A 8/1959 Sieger, Jr. et al.
2,907,327 A 10/1959 White
(Continued)

FOREIGN PATENT DOCUMENTS

DE 1029528 B 5/1958
EP 0146699 A1 7/1985
(Continued)

OTHER PUBLICATIONS

Johnson & Johnson: New Minimally Invasive Breast Biopsy Device Receives Marketing Clearance in Canada; Aug. 6, 1999. From http://www.jnjgateway.com. 4 pages.
(Continued)

*Primary Examiner* — Max F Hindenburg

(57) ABSTRACT

A method of operating a tissue marking apparatus includes providing a tissue marking apparatus having a cannula, a stylet, and an imaging marker, the cannula having a peripheral wall forming a lumen and a lateral opening in the peripheral wall that is open to the lumen, and having a resilient end wall extending downwardly from the peripheral wall at a distal extent of the lateral opening, the stylet being slidably received within the lumen of the cannula for movement in the lumen; moving the stylet in a distal direction to expel the imaging marker from the lateral opening; and continue moving the stylet in the distal direction to deflect the resilient end wall of the cannula such that a distal end of the stylet passes beneath the resilient end wall to substantially close off the lateral opening of the cannula.

12 Claims, 5 Drawing Sheets

Related U.S. Application Data division of application No. 15/078,847, filed on Mar. 23, 2016, now abandoned, which is a continuation of application No. 12/850,844, filed on Aug. 5, 2010, now abandoned, which is a continuation of application No. 11/275,918, filed on Feb. 3, 2006, now Pat. No. 7,819,820, which is a continuation of application No. 10/710,587, filed on Jul. 22, 2004, now abandoned, and a continuation-in-part of application No. 10/707,044, filed on Nov. 17, 2003, now Pat. No. 7,424,320.

(60) Provisional application No. 60/427,048, filed on Nov. 18, 2002.

(56) References Cited

U.S. PATENT DOCUMENTS

| | | |
|---|---|---|
| 3,005,457 A | 10/1961 | Millman |
| 3,128,744 A | 4/1964 | Jefferts et al. |
| 3,402,712 A | 9/1968 | Eisenhand |
| 3,516,412 A | 6/1970 | Ackerman |
| 3,818,894 A | 6/1974 | Wichterle et al. |
| 3,820,545 A | 6/1974 | Jefferts |
| 3,823,212 A | 7/1974 | Chvapil |
| 3,921,632 A | 11/1975 | Bardani |
| 4,005,699 A | 2/1977 | Bucalo |
| 4,007,732 A | 2/1977 | Kvavle et al. |
| 4,041,931 A | 8/1977 | Elliott et al. |
| 4,086,914 A | 5/1978 | Moore |
| 4,103,690 A | 8/1978 | Harris |
| 4,105,030 A | 8/1978 | Kercso |
| 4,127,774 A | 11/1978 | Gillen |
| 4,172,449 A | 10/1979 | LeRoy et al. |
| 4,197,846 A | 4/1980 | Bucalo |
| 4,217,889 A | 8/1980 | Radovan et al. |
| 4,228,799 A | 10/1980 | Anichkov et al. |
| 4,276,885 A | 7/1981 | Tickner et al. |
| 4,294,241 A | 10/1981 | Miyata |
| 4,298,998 A | 11/1981 | Naficy |
| 4,331,654 A | 5/1982 | Morris |
| 4,347,234 A | 8/1982 | Wahlig et al. |
| 4,390,018 A | 6/1983 | Zukowski |
| 4,400,170 A | 8/1983 | McNaughton et al. |
| 4,401,124 A | 8/1983 | Guess et al. |
| 4,405,314 A | 9/1983 | Cope |
| 4,428,082 A | 1/1984 | Naficy |
| 4,438,253 A | 3/1984 | Casey et al. |
| 4,442,843 A | 4/1984 | Rasor et al. |
| 4,470,160 A | 9/1984 | Cavon |
| 4,487,209 A | 12/1984 | Mehl |
| 4,545,367 A | 10/1985 | Tucci |
| 4,582,061 A | 4/1986 | Fry |
| 4,582,640 A | 4/1986 | Smestad et al. |
| 4,588,395 A | 5/1986 | Lemelson |
| 4,597,753 A | 7/1986 | Turley |
| 4,647,480 A | 3/1987 | Ahmed |
| 4,655,226 A | 4/1987 | Lee |
| 4,661,103 A | 4/1987 | Harman |
| 4,682,606 A | 7/1987 | DeCaprio |
| 4,693,237 A | 9/1987 | Hoffman et al. |
| 4,718,433 A | 1/1988 | Feinstein |
| 4,740,208 A | 4/1988 | Cavon |
| 4,762,128 A | 8/1988 | Rosenbluth |
| 4,813,062 A | 3/1989 | Gilpatrick |
| 4,820,267 A | 4/1989 | Harman |
| 4,832,680 A | 5/1989 | Haber et al. |
| 4,832,686 A | 5/1989 | Anderson |
| 4,847,049 A | 7/1989 | Yamamoto |
| 4,863,470 A | 9/1989 | Carter |
| 4,870,966 A | 10/1989 | Dellon et al. |
| 4,874,376 A | 10/1989 | Hawkins, Jr. |
| 4,889,707 A | 12/1989 | Day et al. |
| 4,909,250 A | 3/1990 | Smith |
| 4,931,059 A | 6/1990 | Markham |
| 4,938,763 A | 7/1990 | Dunn et al. |
| 4,950,234 A | 8/1990 | Fujioka et al. |
| 4,950,665 A | 8/1990 | Floyd |
| 4,963,150 A | 10/1990 | Brauman |
| 4,970,298 A | 11/1990 | Silver et al. |
| 4,989,608 A | 2/1991 | Ratner |
| 4,994,013 A | 2/1991 | Suthanthiran et al. |
| 4,994,028 A | 2/1991 | Leonard et al. |
| 5,012,818 A | 5/1991 | Joishy |
| 5,013,090 A | 5/1991 | Matsuura |
| 5,018,530 A | 5/1991 | Rank et al. |
| 5,035,891 A | 7/1991 | Runkel et al. |
| 5,059,197 A | 10/1991 | Urie et al. |
| 5,081,997 A | 1/1992 | Bosley, Jr. et al. |
| 5,120,802 A | 6/1992 | Mares et al. |
| 5,125,413 A | 6/1992 | Baran |
| 5,137,928 A | 8/1992 | Erbel et al. |
| 5,141,748 A | 8/1992 | Rizzo |
| 5,147,295 A | 9/1992 | Stewart |
| 5,147,307 A | 9/1992 | Gluck |
| 5,147,631 A | 9/1992 | Glajch et al. |
| 5,162,430 A | 11/1992 | Rhee et al. |
| 5,163,896 A | 11/1992 | Suthanthiran et al. |
| 5,195,540 A | 3/1993 | Shiber |
| 5,197,482 A | 3/1993 | Rank et al. |
| 5,199,441 A | 4/1993 | Hogle |
| 5,201,704 A | 4/1993 | Ray |
| 5,219,339 A | 6/1993 | Saito |
| 5,221,269 A | 6/1993 | Miller et al. |
| 5,234,426 A | 8/1993 | Rank et al. |
| 5,236,410 A | 8/1993 | Granov et al. |
| 5,242,759 A | 9/1993 | Hall |
| 5,250,026 A | 10/1993 | Ehrlich et al. |
| 5,271,961 A | 12/1993 | Mathiowitz et al. |
| 5,273,532 A | 12/1993 | Niezink et al. |
| 5,280,788 A | 1/1994 | Janes et al. |
| 5,281,197 A | 1/1994 | Arias et al. |
| 5,281,408 A | 1/1994 | Unger |
| 5,282,781 A | 2/1994 | Liprie |
| 5,284,479 A | 2/1994 | de Jong |
| 5,289,831 A | 3/1994 | Bosley |
| 5,290,310 A | 3/1994 | Makower et al. |
| 5,312,435 A | 5/1994 | Nash et al. |
| 5,320,100 A | 6/1994 | Herweck et al. |
| 5,320,613 A | 6/1994 | Houge et al. |
| 5,328,955 A | 7/1994 | Rhee et al. |
| 5,334,216 A | 8/1994 | Vidal et al. |
| 5,334,381 A | 8/1994 | Unger |
| 5,344,640 A | 9/1994 | Deutsch et al. |
| 5,353,804 A | 10/1994 | Kornberg et al. |
| 5,354,623 A | 10/1994 | Hall |
| 5,358,514 A | 10/1994 | Schulman et al. |
| 5,360,416 A | 11/1994 | Ausherman et al. |
| 5,366,756 A | 11/1994 | Chesterfield et al. |
| 5,368,030 A | 11/1994 | Zinreich et al. |
| 5,388,588 A | 2/1995 | Nabai et al. |
| 5,394,875 A | 3/1995 | Lewis et al. |
| 5,395,319 A | 3/1995 | Hirsch et al. |
| 5,405,402 A | 4/1995 | Dye et al. |
| 5,409,004 A | 4/1995 | Sloan |
| 5,417,708 A | 5/1995 | Hall et al. |
| 5,422,730 A | 6/1995 | Barlow et al. |
| 5,425,366 A | 6/1995 | Reinhardt et al. |
| 5,431,639 A | 7/1995 | Shaw |
| 5,433,204 A | 7/1995 | Olson |
| 5,449,560 A | 9/1995 | Antheunis et al. |
| 5,451,406 A | 9/1995 | Lawin et al. |
| 5,458,643 A | 10/1995 | Oka et al. |
| 5,460,182 A | 10/1995 | Goodman et al. |
| 5,469,847 A | 11/1995 | Zinreich et al. |
| 5,475,052 A | 12/1995 | Rhee et al. |
| 5,490,521 A | 2/1996 | Davis et al. |
| 5,494,030 A | 2/1996 | Swartz et al. |
| 5,499,989 A | 3/1996 | LaBash |
| 5,507,807 A | 4/1996 | Shippert |
| 5,508,021 A | 4/1996 | Grinstaff et al. |
| 5,514,085 A | 5/1996 | Yoon |
| 5,522,896 A | 6/1996 | Prescott |
| 5,538,726 A | 7/1996 | Order |

(56) References Cited

U.S. PATENT DOCUMENTS

| | | |
|---|---|---|
| 5,542,915 A | 8/1996 | Edwards et al. |
| 5,545,180 A | 8/1996 | Le et al. |
| 5,549,560 A | 8/1996 | Van de Wijdeven |
| 5,567,413 A | 10/1996 | Klaveness et al. |
| RE35,391 E | 12/1996 | Brauman |
| 5,580,568 A | 12/1996 | Greff et al. |
| 5,585,112 A | 12/1996 | Unger et al. |
| 5,611,352 A | 3/1997 | Kobren et al. |
| 5,626,611 A | 5/1997 | Liu et al. |
| 5,628,781 A | 5/1997 | Williams et al. |
| 5,629,008 A | 5/1997 | Lee |
| 5,636,255 A | 6/1997 | Ellis |
| 5,643,246 A | 7/1997 | Leeb et al. |
| 5,646,146 A | 7/1997 | Faarup et al. |
| 5,651,772 A | 7/1997 | Arnett |
| 5,657,366 A | 8/1997 | Nakayama |
| 5,665,092 A | 9/1997 | Mangiardi et al. |
| 5,667,767 A | 9/1997 | Greff et al. |
| 5,669,882 A | 9/1997 | Pyles |
| 5,673,841 A | 10/1997 | Schulze et al. |
| 5,676,146 A | 10/1997 | Scarborough |
| 5,676,925 A | 10/1997 | Klaveness et al. |
| 5,688,490 A | 11/1997 | Tournier et al. |
| 5,690,120 A | 11/1997 | Jacobsen et al. |
| 5,695,480 A | 12/1997 | Evans et al. |
| 5,702,128 A | 12/1997 | Maxim et al. |
| 5,702,682 A | 12/1997 | Thompson |
| 5,702,716 A | 12/1997 | Dunn et al. |
| 5,716,981 A | 2/1998 | Hunter et al. |
| 5,747,060 A | 5/1998 | Sackler et al. |
| 5,749,887 A | 5/1998 | Heske et al. |
| 5,752,974 A | 5/1998 | Rhee et al. |
| 5,762,903 A | 6/1998 | Park et al. |
| 5,769,086 A | 6/1998 | Ritchart et al. |
| 5,776,496 A | 7/1998 | Violante et al. |
| 5,779,647 A | 7/1998 | Chau et al. |
| 5,782,764 A | 7/1998 | Werne |
| 5,782,771 A | 7/1998 | Hussman |
| 5,782,775 A | 7/1998 | Milliman et al. |
| 5,795,308 A | 8/1998 | Russin |
| 5,799,099 A | 8/1998 | Wang et al. |
| 5,800,362 A | 9/1998 | Kobren et al. |
| 5,800,389 A | 9/1998 | Burney et al. |
| 5,800,445 A | 9/1998 | Ratcliff et al. |
| 5,800,541 A | 9/1998 | Rhee et al. |
| 5,810,884 A | 9/1998 | Kim |
| 5,817,022 A | 10/1998 | Vesely |
| 5,820,918 A | 10/1998 | Ronan et al. |
| 5,821,184 A | 10/1998 | Haines et al. |
| 5,823,198 A | 10/1998 | Jones et al. |
| 5,824,042 A | 10/1998 | Lombardi et al. |
| 5,824,081 A | 10/1998 | Knapp et al. |
| 5,826,776 A | 10/1998 | Schulze et al. |
| 5,830,178 A | 11/1998 | Jones et al. |
| 5,830,222 A | 11/1998 | Makower |
| 5,842,477 A | 12/1998 | Naughton et al. |
| 5,842,999 A | 12/1998 | Pruitt et al. |
| 5,845,646 A | 12/1998 | Lemelson |
| 5,846,220 A | 12/1998 | Elsberry |
| 5,851,508 A | 12/1998 | Greff et al. |
| 5,853,366 A | 12/1998 | Dowlatshahi |
| 5,865,806 A | 2/1999 | Howell |
| 5,869,080 A | 2/1999 | McGregor et al. |
| 5,871,501 A | 2/1999 | Leschinsky et al. |
| 5,876,340 A | 3/1999 | Tu et al. |
| 5,879,357 A | 3/1999 | Heaton et al. |
| 5,891,558 A | 4/1999 | Bell et al. |
| 5,897,507 A | 4/1999 | Kortenbach et al. |
| 5,902,310 A | 5/1999 | Foerster et al. |
| 5,911,705 A | 6/1999 | Howell |
| 5,916,164 A | 6/1999 | Fitzpatrick et al. |
| 5,921,933 A | 7/1999 | Sarkis et al. |
| 5,922,024 A | 7/1999 | Janzen et al. |
| 5,928,626 A | 7/1999 | Klaveness et al. |
| 5,928,773 A | 7/1999 | Andersen |
| 5,941,439 A | 8/1999 | Kammerer et al. |
| 5,941,890 A | 8/1999 | Voegele et al. |
| 5,942,209 A | 8/1999 | Leavitt et al. |
| 5,948,425 A | 9/1999 | Janzen et al. |
| 5,954,670 A | 9/1999 | Baker |
| 5,972,817 A | 10/1999 | Haines et al. |
| 5,976,146 A | 11/1999 | Ogawa et al. |
| 5,980,564 A | 11/1999 | Stinson |
| 5,989,265 A | 11/1999 | Bouquet De La Joliniere et al. |
| 6,015,541 A | 1/2000 | Greff et al. |
| 6,027,471 A | 2/2000 | Fallon et al. |
| 6,030,333 A | 2/2000 | Sioshansi et al. |
| 6,053,925 A | 4/2000 | Barnhart |
| 6,056,700 A | 5/2000 | Burney et al. |
| 6,066,122 A | 5/2000 | Fisher |
| 6,066,325 A | 5/2000 | Wallace et al. |
| 6,071,301 A | 6/2000 | Cragg et al. |
| 6,071,310 A | 6/2000 | Picha et al. |
| 6,071,496 A | 6/2000 | Stein et al. |
| 6,090,996 A | 7/2000 | Li |
| 6,096,065 A | 8/2000 | Crowley |
| 6,096,070 A | 8/2000 | Ragheb et al. |
| 6,106,473 A | 8/2000 | Violante et al. |
| 6,117,108 A | 9/2000 | Woehr et al. |
| 6,120,536 A | 9/2000 | Ding et al. |
| 6,135,993 A | 10/2000 | Hussman |
| 6,142,955 A | 11/2000 | Farascioni et al. |
| 6,159,240 A | 12/2000 | Sparer et al. |
| 6,159,445 A | 12/2000 | Klaveness et al. |
| 6,161,034 A | 12/2000 | Burbank et al. |
| 6,162,192 A | 12/2000 | Cragg et al. |
| 6,166,079 A | 12/2000 | Follen et al. |
| 6,173,715 B1 | 1/2001 | Sinanan et al. |
| 6,174,330 B1 | 1/2001 | Stinson |
| 6,177,062 B1 | 1/2001 | Stein et al. |
| 6,181,960 B1 | 1/2001 | Jensen et al. |
| 6,183,497 B1 | 2/2001 | Sing et al. |
| 6,190,350 B1 | 2/2001 | Davis et al. |
| 6,190,353 B1 | 2/2001 | Makower et al. |
| 6,200,258 B1 | 3/2001 | Slater et al. |
| 6,203,507 B1 | 3/2001 | Wadsworth et al. |
| 6,203,524 B1 | 3/2001 | Burney et al. |
| 6,203,568 B1 | 3/2001 | Lombardi et al. |
| 6,213,957 B1 | 4/2001 | Milliman et al. |
| 6,214,045 B1 | 4/2001 | Corbitt, Jr. et al. |
| 6,214,315 B1 | 4/2001 | Greff et al. |
| 6,220,248 B1 | 4/2001 | Voegele et al. |
| 6,224,630 B1 | 5/2001 | Bao et al. |
| 6,228,049 B1 | 5/2001 | Schroeder et al. |
| 6,228,055 B1 | 5/2001 | Foerster et al. |
| 6,231,615 B1 | 5/2001 | Preissman |
| 6,234,177 B1 | 5/2001 | Barsch |
| 6,241,687 B1 | 6/2001 | Voegele et al. |
| 6,241,734 B1 | 6/2001 | Scribner et al. |
| 6,251,135 B1 | 6/2001 | Stinson et al. |
| 6,251,418 B1 | 6/2001 | Ahern et al. |
| 6,261,243 B1 | 7/2001 | Burney et al. |
| 6,261,302 B1 | 7/2001 | Voegele et al. |
| 6,264,917 B1 | 7/2001 | Klaveness et al. |
| 6,270,464 B1 | 8/2001 | Fulton, III et al. |
| 6,270,472 B1 | 8/2001 | Antaki et al. |
| 6,287,278 B1 | 9/2001 | Woehr et al. |
| 6,287,332 B1 | 9/2001 | Bolz et al. |
| 6,289,229 B1 | 9/2001 | Crowley |
| 6,306,154 B1 | 10/2001 | Hudson et al. |
| 6,312,429 B1 | 11/2001 | Burbank et al. |
| 6,316,522 B1 | 11/2001 | Loomis et al. |
| 6,325,789 B1 | 12/2001 | Janzen et al. |
| 6,335,029 B1 | 1/2002 | Kamath et al. |
| 6,336,904 B1 | 1/2002 | Nikolchev |
| 6,340,367 B1 | 1/2002 | Stinson et al. |
| 6,343,227 B1 | 1/2002 | Crowley |
| 6,347,240 B1 | 2/2002 | Foley et al. |
| 6,347,241 B2 | 2/2002 | Burbank et al. |
| 6,350,244 B1 | 2/2002 | Fisher |
| 6,350,274 B1 | 2/2002 | Li |
| 6,354,989 B1 | 3/2002 | Nudeshima |
| 6,356,112 B1 | 3/2002 | Tran et al. |
| 6,356,782 B1 | 3/2002 | Sirimanne et al. |

(56) References Cited

U.S. PATENT DOCUMENTS

| | | | |
|---|---|---|---|
| 6,358,217 | B1 | 3/2002 | Bourassa |
| 6,363,940 | B1 | 4/2002 | Krag |
| 6,371,904 | B1 | 4/2002 | Sirimanne et al. |
| 6,394,965 | B1 | 5/2002 | Klein |
| 6,403,758 | B1 | 6/2002 | Loomis |
| 6,405,733 | B1 | 6/2002 | Fogarty et al. |
| 6,409,742 | B1 | 6/2002 | Fulton, III et al. |
| 6,419,621 | B1 | 7/2002 | Sioshansi et al. |
| 6,424,857 | B1 | 7/2002 | Henrichs et al. |
| 6,425,903 | B1 | 7/2002 | Voegele |
| 6,427,081 | B1 | 7/2002 | Burbank et al. |
| 6,436,030 | B2 | 8/2002 | Rehil |
| 6,447,524 | B1 | 9/2002 | Knodel et al. |
| 6,447,527 | B1 | 9/2002 | Thompson et al. |
| 6,450,937 | B1 | 9/2002 | Mercereau et al. |
| 6,450,938 | B1 | 9/2002 | Miller |
| 6,471,700 | B1 | 10/2002 | Burbank et al. |
| 6,478,790 | B2 | 11/2002 | Bardani |
| 6,506,156 | B1 | 1/2003 | Jones et al. |
| 6,511,468 | B1 | 1/2003 | Cragg et al. |
| 6,511,650 | B1 | 1/2003 | Eiselt et al. |
| 6,537,193 | B1 | 3/2003 | Lennox |
| 6,540,981 | B2 | 4/2003 | Klaveness et al. |
| 6,544,185 | B2 | 4/2003 | Montegrande |
| 6,544,231 | B1 | 4/2003 | Palmer et al. |
| 6,544,269 | B2 | 4/2003 | Osborne et al. |
| 6,551,253 | B2 | 4/2003 | Worm et al. |
| 6,554,760 | B2 | 4/2003 | Lamoureux et al. |
| 6,562,317 | B2 | 5/2003 | Greff et al. |
| 6,564,806 | B1 | 5/2003 | Fogarty et al. |
| 6,565,551 | B1 | 5/2003 | Jones et al. |
| 6,567,689 | B2 | 5/2003 | Burbank et al. |
| 6,575,888 | B2 | 6/2003 | Zamora et al. |
| 6,575,991 | B1 | 6/2003 | Chesbrough et al. |
| 6,585,773 | B1 | 7/2003 | Xie |
| 6,605,047 | B2 | 8/2003 | Zarins et al. |
| 6,610,026 | B2 | 8/2003 | Cragg et al. |
| 6,613,002 | B1 | 9/2003 | Clark et al. |
| 6,616,630 | B1 | 9/2003 | Woehr et al. |
| 6,626,850 | B1 | 9/2003 | Chau et al. |
| 6,626,899 | B2 | 9/2003 | Houser et al. |
| 6,628,982 | B1 | 9/2003 | Thomas et al. |
| 6,629,947 | B1 | 10/2003 | Sahatjian et al. |
| 6,636,758 | B2 | 10/2003 | Sanchez et al. |
| 6,638,234 | B2 | 10/2003 | Burbank et al. |
| 6,638,308 | B2 | 10/2003 | Corbitt, Jr. et al. |
| 6,652,442 | B2 | 11/2003 | Gatto |
| 6,656,192 | B2 | 12/2003 | Espositio et al. |
| 6,659,933 | B2 | 12/2003 | Asano |
| 6,662,041 | B2 | 12/2003 | Burbank et al. |
| 6,699,205 | B2 | 3/2004 | Fulton, III et al. |
| 6,712,774 | B2 | 3/2004 | Voegele et al. |
| 6,712,836 | B1 | 3/2004 | Berg et al. |
| 6,716,444 | B1 | 4/2004 | Castro et al. |
| 6,725,083 | B1 | 4/2004 | Burbank et al. |
| 6,730,042 | B2 | 5/2004 | Fulton et al. |
| 6,730,044 | B2 | 5/2004 | Stephens et al. |
| 6,746,661 | B2 | 6/2004 | Kaplan |
| 6,746,773 | B2 | 6/2004 | Llanos et al. |
| 6,752,154 | B2 | 6/2004 | Fogarty et al. |
| 6,766,186 | B1 | 7/2004 | Hoyns et al. |
| 6,774,278 | B1 | 8/2004 | Ragheb et al. |
| 6,780,179 | B2 | 8/2004 | Lee et al. |
| 6,824,507 | B2 | 11/2004 | Miller |
| 6,824,527 | B2 | 11/2004 | Gollobin |
| 6,846,320 | B2 | 1/2005 | Ashby et al. |
| 6,862,470 | B2 | 3/2005 | Burbank et al. |
| 6,863,685 | B2 | 3/2005 | Davila et al. |
| 6,881,226 | B2 | 4/2005 | Corbitt, Jr. et al. |
| 6,889,833 | B2 | 5/2005 | Seiler et al. |
| 6,899,731 | B2 | 5/2005 | Li et al. |
| 6,918,927 | B2 | 7/2005 | Bates et al. |
| 6,936,014 | B2 | 8/2005 | Vetter et al. |
| 6,939,318 | B2 | 9/2005 | Stenzel |
| 6,945,973 | B2 | 9/2005 | Bray |
| 6,951,564 | B2 | 10/2005 | Espositio et al. |
| 6,958,044 | B2 | 10/2005 | Burbank et al. |
| 6,992,233 | B2 | 1/2006 | Drake et al. |
| 6,993,375 | B2 | 1/2006 | Burbank et al. |
| 6,994,712 | B1 | 2/2006 | Fisher et al. |
| 6,996,433 | B2 | 2/2006 | Burbank et al. |
| 7,001,341 | B2 | 2/2006 | Gellman et al. |
| 7,008,382 | B2 | 3/2006 | Adams et al. |
| 7,014,610 | B2 | 3/2006 | Koulik |
| 7,025,765 | B2 | 4/2006 | Balbierz et al. |
| 7,044,957 | B2 | 5/2006 | Foerster et al. |
| 7,047,063 | B2 | 5/2006 | Burbank et al. |
| 7,083,576 | B2 | 8/2006 | Zarins et al. |
| 7,125,397 | B2 | 10/2006 | Woehr et al. |
| 7,135,978 | B2 | 11/2006 | Gisselberg et al. |
| 7,160,258 | B2 | 1/2007 | Imran et al. |
| 7,172,549 | B2 | 2/2007 | Slater et al. |
| 7,189,206 | B2 | 3/2007 | Quick et al. |
| 7,214,211 | B2 | 5/2007 | Woehr et al. |
| 7,229,417 | B2 | 6/2007 | Foerster et al. |
| 7,236,816 | B2 | 6/2007 | Kumar et al. |
| 7,264,613 | B2 | 9/2007 | Woehr et al. |
| 7,280,865 | B2 | 10/2007 | Adler |
| 7,294,118 | B2 | 11/2007 | Saulenas et al. |
| 7,297,725 | B2 | 11/2007 | Winterton et al. |
| 7,329,402 | B2 | 2/2008 | Unger et al. |
| 7,329,414 | B2 | 2/2008 | Fisher et al. |
| 7,407,054 | B2 | 8/2008 | Seiler et al. |
| 7,416,533 | B2 | 8/2008 | Gellman et al. |
| 7,424,320 | B2 | 9/2008 | Chesbrough et al. |
| 7,449,000 | B2 | 11/2008 | Adams et al. |
| 7,527,610 | B2 | 5/2009 | Erickson |
| 7,534,452 | B2 | 5/2009 | Chernomorsky et al. |
| 7,535,363 | B2 | 5/2009 | Gisselberg et al. |
| 7,565,191 | B2 | 7/2009 | Burbank et al. |
| 7,569,065 | B2 | 8/2009 | Chesbrough et al. |
| 7,577,473 | B2 | 8/2009 | Davis et al. |
| 7,637,948 | B2 | 12/2009 | Corbitt, Jr. |
| 7,651,505 | B2 | 1/2010 | Lubock et al. |
| 7,668,582 | B2 | 2/2010 | Sirimanne et al. |
| 7,670,350 | B2 | 3/2010 | Selis |
| 7,783,336 | B2 | 8/2010 | Macfarlane et al. |
| 7,792,569 | B2 | 9/2010 | Burbank et al. |
| 7,819,819 | B2 | 10/2010 | Quick et al. |
| 7,819,820 | B2 | 10/2010 | Field et al. |
| 7,844,319 | B2 | 11/2010 | Susil et al. |
| 7,871,438 | B2 | 1/2011 | Corbitt, Jr. |
| 7,877,133 | B2 | 1/2011 | Burbank et al. |
| 7,914,553 | B2 | 3/2011 | Ferree |
| 7,945,307 | B2 | 5/2011 | Lubock et al. |
| 7,983,734 | B2 | 7/2011 | Jones et al. |
| 8,011,508 | B2 | 9/2011 | Seiler et al. |
| 8,027,712 | B2 | 9/2011 | Sioshansi et al. |
| 8,052,658 | B2 | 11/2011 | Field |
| 8,052,708 | B2 | 11/2011 | Chesbrough et al. |
| 8,064,987 | B2 | 11/2011 | Carr, Jr. |
| 8,128,641 | B2 | 3/2012 | Wardle |
| 8,157,862 | B2 | 4/2012 | Corbitt, Jr. |
| 8,177,792 | B2 | 5/2012 | Lubock et al. |
| 8,306,602 | B2 | 11/2012 | Sirimanne et al. |
| 8,320,993 | B2 | 11/2012 | Sirimanne et al. |
| 8,320,994 | B2 | 11/2012 | Sirimanne et al. |
| 8,361,082 | B2 | 1/2013 | Jones et al. |
| 8,401,622 | B2 | 3/2013 | Talpade et al. |
| 8,579,931 | B2 | 11/2013 | Chesbrough et al. |
| 8,626,269 | B2 | 1/2014 | Jones et al. |
| 8,626,270 | B2 | 1/2014 | Burbank et al. |
| 8,639,315 | B2 | 1/2014 | Burbank et al. |
| 8,668,737 | B2 | 3/2014 | Corbitt, Jr. |
| 8,680,498 | B2 | 3/2014 | Corbitt et al. |
| 8,718,745 | B2 | 5/2014 | Burbank et al. |
| 8,784,433 | B2 | 7/2014 | Lubock et al. |
| 8,965,486 | B2 | 2/2015 | Burbank et al. |
| 9,044,162 | B2 | 6/2015 | Jones et al. |
| 9,149,341 | B2 | 10/2015 | Jones et al. |
| 9,237,937 | B2 | 1/2016 | Burbank et al. |
| 9,480,554 | B2 | 11/2016 | Corbitt, Jr. et al. |
| 9,861,294 | B2 | 1/2018 | Jones et al. |
| 2001/0006616 | A1 | 7/2001 | Leavitt et al. |

(56) References Cited

U.S. PATENT DOCUMENTS

| | | |
|---|---|---|
| 2002/0004060 A1 | 1/2002 | Heublein et al. |
| 2002/0016625 A1 | 2/2002 | Falotico et al. |
| 2002/0022883 A1 | 2/2002 | Burg |
| 2002/0026201 A1 | 2/2002 | Foerster et al. |
| 2002/0044969 A1 | 4/2002 | Harden et al. |
| 2002/0045842 A1 | 4/2002 | Van Bladel et al. |
| 2002/0052572 A1 | 5/2002 | Franco et al. |
| 2002/0055731 A1 | 5/2002 | Atala et al. |
| 2002/0058868 A1 | 5/2002 | Hoshino et al. |
| 2002/0058882 A1 | 5/2002 | Fulton, III et al. |
| 2002/0077687 A1 | 6/2002 | Ahn |
| 2002/0082517 A1 | 6/2002 | Klein |
| 2002/0082519 A1 | 6/2002 | Miller et al. |
| 2002/0082682 A1 | 6/2002 | Barclay et al. |
| 2002/0082683 A1 | 6/2002 | Stinson et al. |
| 2002/0095204 A1 | 7/2002 | Thompson et al. |
| 2002/0095205 A1 | 7/2002 | Edwin et al. |
| 2002/0107437 A1 | 8/2002 | Sirimanne et al. |
| 2002/0133148 A1 | 9/2002 | Daniel et al. |
| 2002/0143359 A1 | 10/2002 | Fulton, III et al. |
| 2002/0165608 A1 | 11/2002 | Llanos et al. |
| 2002/0177776 A1 | 11/2002 | Crawford Kellar et al. |
| 2002/0188195 A1 | 12/2002 | Mills |
| 2002/0193815 A1 | 12/2002 | Foerster et al. |
| 2002/0193867 A1 | 12/2002 | Gladdish, Jr. et al. |
| 2003/0032969 A1 | 2/2003 | Gannoe et al. |
| 2003/0036803 A1 | 2/2003 | McGhan |
| 2003/0051735 A1 | 3/2003 | Pavcnik et al. |
| 2003/0116806 A1 | 6/2003 | Kato |
| 2003/0165478 A1 | 9/2003 | Sokoll |
| 2003/0191355 A1 | 10/2003 | Ferguson |
| 2003/0199887 A1 | 10/2003 | Ferrera et al. |
| 2003/0225420 A1 | 12/2003 | Wardle |
| 2003/0236573 A1 | 12/2003 | Evans et al. |
| 2004/0001841 A1 | 1/2004 | Nagavarapu et al. |
| 2004/0002650 A1 | 1/2004 | Mandrusov et al. |
| 2004/0016195 A1 | 1/2004 | Archuleta |
| 2004/0024304 A1 | 2/2004 | Foerster et al. |
| 2004/0059341 A1 | 3/2004 | Gellman et al. |
| 2004/0068312 A1 | 4/2004 | Sigg et al. |
| 2004/0073284 A1 | 4/2004 | Bates et al. |
| 2004/0097981 A1 | 5/2004 | Selis |
| 2004/0101479 A1 | 5/2004 | Burbank et al. |
| 2004/0101548 A1 | 5/2004 | Pendharkar |
| 2004/0106891 A1 | 6/2004 | Langan et al. |
| 2004/0116802 A1 | 6/2004 | Jessop et al. |
| 2004/0127765 A1 | 7/2004 | Seiler et al. |
| 2004/0133124 A1 | 7/2004 | Bates et al. |
| 2004/0153074 A1 | 8/2004 | Bojarski et al. |
| 2004/0162574 A1 | 8/2004 | Viola |
| 2004/0167619 A1 | 8/2004 | Case et al. |
| 2004/0204660 A1 | 10/2004 | Fulton et al. |
| 2004/0210208 A1 | 10/2004 | Paul et al. |
| 2004/0213756 A1 | 10/2004 | Michal et al. |
| 2004/0236213 A1 | 11/2004 | Jones et al. |
| 2004/0253185 A1 | 12/2004 | Herweck et al. |
| 2004/0265371 A1 | 12/2004 | Looney et al. |
| 2005/0019262 A1 | 1/2005 | Chernomorsky et al. |
| 2005/0020916 A1 | 1/2005 | MacFarlane et al. |
| 2005/0033157 A1 | 2/2005 | Klien et al. |
| 2005/0033195 A1 | 2/2005 | Fulton et al. |
| 2005/0036946 A1 | 2/2005 | Pathak et al. |
| 2005/0045192 A1 | 3/2005 | Fulton et al. |
| 2005/0059887 A1 | 3/2005 | Mostafavi et al. |
| 2005/0059888 A1 | 3/2005 | Sirimanne et al. |
| 2005/0065354 A1 | 3/2005 | Roberts |
| 2005/0065453 A1 | 3/2005 | Shabaz et al. |
| 2005/0080337 A1 | 4/2005 | Sirimanne et al. |
| 2005/0080339 A1 | 4/2005 | Sirimanne et al. |
| 2005/0100580 A1 | 5/2005 | Osborne et al. |
| 2005/0112151 A1 | 5/2005 | Horng |
| 2005/0113659 A1 | 5/2005 | Pothier et al. |
| 2005/0119562 A1 | 6/2005 | Jones et al. |
| 2005/0142161 A1 | 6/2005 | Freeman et al. |
| 2005/0143650 A1 | 6/2005 | Winkel |
| 2005/0165305 A1 | 7/2005 | Foerster et al. |
| 2005/0175657 A1 | 8/2005 | Hunter et al. |
| 2005/0181007 A1 | 8/2005 | Hunter et al. |
| 2005/0208122 A1 | 9/2005 | Allen et al. |
| 2005/0234336 A1 | 10/2005 | Beckman et al. |
| 2005/0268922 A1 | 12/2005 | Conrad et al. |
| 2005/0273002 A1 | 12/2005 | Goosen et al. |
| 2005/0277871 A1 | 12/2005 | Selis |
| 2006/0004440 A1 | 1/2006 | Stinson |
| 2006/0009800 A1 | 1/2006 | Christianson et al. |
| 2006/0025677 A1 | 2/2006 | Verard et al. |
| 2006/0025795 A1 | 2/2006 | Chesbrough et al. |
| 2006/0036158 A1 | 2/2006 | Field et al. |
| 2006/0036159 A1 | 2/2006 | Sirimanne et al. |
| 2006/0074443 A1 | 4/2006 | Foerster et al. |
| 2006/0079770 A1 | 4/2006 | Sirimanne et al. |
| 2006/0079805 A1 | 4/2006 | Miller et al. |
| 2006/0079829 A1 | 4/2006 | Fulton et al. |
| 2006/0079888 A1 | 4/2006 | Mulier et al. |
| 2006/0122503 A1 | 6/2006 | Burbank et al. |
| 2006/0155190 A1 | 7/2006 | Burbank et al. |
| 2006/0173280 A1 | 8/2006 | Goosen et al. |
| 2006/0173296 A1 | 8/2006 | Miller et al. |
| 2006/0177379 A1 | 8/2006 | Asgari |
| 2006/0217635 A1 | 9/2006 | McCombs et al. |
| 2006/0235298 A1 | 10/2006 | Kotmel et al. |
| 2006/0241385 A1 | 10/2006 | Dietz |
| 2006/0241411 A1 | 10/2006 | Field et al. |
| 2006/0292690 A1 | 12/2006 | Liu et al. |
| 2007/0021642 A1 | 1/2007 | Lamoureux et al. |
| 2007/0038145 A1 | 2/2007 | Field |
| 2007/0083132 A1 | 4/2007 | Sharrow |
| 2007/0106152 A1 | 5/2007 | Kantrowitz et al. |
| 2007/0135711 A1 | 6/2007 | Chernomorsky et al. |
| 2007/0142725 A1 | 6/2007 | Hardin et al. |
| 2007/0167736 A1 | 7/2007 | Dietz et al. |
| 2007/0167749 A1 | 7/2007 | Yarnall et al. |
| 2007/0239118 A1 | 10/2007 | Ono et al. |
| 2007/0287933 A1 | 12/2007 | Phan et al. |
| 2008/0039819 A1 | 2/2008 | Jones et al. |
| 2008/0091120 A1 | 4/2008 | Fisher |
| 2008/0097199 A1 | 4/2008 | Mullen |
| 2008/0188768 A1 | 8/2008 | Zarins et al. |
| 2008/0269638 A1 | 10/2008 | Cooke et al. |
| 2008/0294039 A1 | 11/2008 | Jones et al. |
| 2009/0000629 A1 | 1/2009 | Hornscheidt et al. |
| 2009/0024225 A1 | 1/2009 | Stubbs |
| 2009/0030309 A1 | 1/2009 | Jones et al. |
| 2009/0069713 A1 | 3/2009 | Adams et al. |
| 2009/0076484 A1 | 3/2009 | Fukaya |
| 2009/0131825 A1 | 5/2009 | Burbank et al. |
| 2009/0171198 A1 | 7/2009 | Jones et al. |
| 2009/0216118 A1 | 8/2009 | Jones et al. |
| 2009/0287078 A1 | 11/2009 | Burbank et al. |
| 2010/0010342 A1 | 1/2010 | Burbank et al. |
| 2010/0030072 A1 | 2/2010 | Casanova et al. |
| 2010/0082102 A1 | 4/2010 | Govil et al. |
| 2010/0198059 A1 | 8/2010 | Burbank et al. |
| 2010/0204570 A1 | 8/2010 | Lubock |
| 2010/0298696 A1 | 11/2010 | Field et al. |
| 2010/0324416 A1 | 12/2010 | Burbank et al. |
| 2011/0092815 A1 | 4/2011 | Burbank et al. |
| 2011/0184280 A1 | 7/2011 | Jones et al. |
| 2012/0078092 A1 | 3/2012 | Jones et al. |
| 2012/0179251 A1 | 7/2012 | Corbitt, Jr. |
| 2013/0144157 A1 | 6/2013 | Jones et al. |
| 2013/0281847 A1 | 10/2013 | Jones et al. |
| 2013/0310686 A1 | 11/2013 | Jones et al. |
| 2014/0058258 A1 | 2/2014 | Chesbrough et al. |
| 2014/0114186 A1 | 4/2014 | Burbank et al. |
| 2014/0142696 A1 | 5/2014 | Corbitt, Jr. |
| 2014/0243675 A1 | 8/2014 | Burbank et al. |
| 2016/0120510 A1 | 5/2016 | Burbank et al. |
| 2016/0128797 A1 | 5/2016 | Burbank et al. |
| 2016/0199150 A1 | 7/2016 | Field et al. |

(56) References Cited

U.S. PATENT DOCUMENTS

FOREIGN PATENT DOCUMENTS

| | | | |
|---|---|---|---|
| EP | 0255123 | A2 | 2/1988 |
| EP | 0292936 | A2 | 11/1988 |
| EP | 0458745 | A1 | 11/1991 |
| EP | 0475077 | A2 | 3/1992 |
| EP | 0552924 | A1 | 7/1993 |
| EP | 0769281 | A2 | 4/1997 |
| EP | 1114618 | A2 | 7/2001 |
| EP | 1163888 | A1 | 12/2001 |
| EP | 1281416 | A2 | 6/2002 |
| EP | 1364628 | A1 | 11/2003 |
| EP | 1493451 | A1 | 1/2005 |
| EP | 1767167 | A2 | 3/2007 |
| FR | 2646674 | A3 | 11/1990 |
| FR | 2853521 | A1 | 10/2004 |
| GB | 708148 | | 4/1954 |
| JP | 2131757 | A | 5/1990 |
| JP | 2006516468 | A | 7/2006 |
| WO | 8906978 | A1 | 8/1989 |
| WO | 9112823 | A1 | 9/1991 |
| WO | 9314712 | A1 | 8/1993 |
| WO | 9317671 | A1 | 9/1993 |
| WO | 9317718 | A1 | 9/1993 |
| WO | 9416647 | A1 | 8/1994 |
| WO | 9507057 | A1 | 3/1995 |
| WO | 9806346 | A1 | 2/1998 |
| WO | 9908607 | A1 | 2/1999 |
| WO | 9935966 | A1 | 7/1999 |
| WO | 951143 | A1 | 10/1999 |
| WO | 0023124 | A1 | 4/2000 |
| WO | 0024332 | A1 | 5/2000 |
| WO | 0028554 | A1 | 5/2000 |
| WO | 0054689 | A1 | 9/2000 |
| WO | 0108578 | A1 | 2/2001 |
| WO | 0170114 | A1 | 9/2001 |
| WO | 0207786 | A2 | 1/2002 |
| WO | 0241786 | A2 | 5/2002 |
| WO | 03000308 | A1 | 1/2003 |
| WO | 2004045444 | A2 | 6/2004 |
| WO | 2005013832 | A1 | 2/2005 |
| WO | 2005089664 | A1 | 9/2005 |
| WO | 2006056739 | A2 | 6/2006 |
| WO | 2006097331 | A2 | 9/2006 |
| WO | 2006105353 | A2 | 10/2006 |
| WO | 2007069105 | A2 | 6/2007 |
| WO | 2008077081 | A2 | 6/2008 |

OTHER PUBLICATIONS

Johnson & Johnson: Mammotome Hand Held Receives FDA Marketing Clearance for Minimally Invasive Breast Biopises; Sep. 1, 1999. From From http://www.jnjgateway.com. 5 pages.

Liberman, Laura, et al. Percutaneous Removal of Malignant Mammographic Lesions at Stereotactic Vacuum-assisted Biopsy. From: The Departments of Radiology, Pathology, and Surgery. Memorial Sloan-Kettering Cancer Center. From the 1997 RSNA scientific assembly. vol. 206, No. 3. pp. 711-715.

Crook, et al. (Prostate Motion During Standard Radiotherapy As Assessed By Fiducial Markers, 1995, Radiotherapy and Oncology 37:35-42.).

Zmora, et al. (Tailoring the pore architecture in 3-D alginate scaffolds by controlling the freezing regime during fabrication, 2001, Elsevier Science Ltd.).

Madihally, et al. (Porous chitosan scaffolds for tissue engineering, 1998, Elsevier Science Ltd.).

Fajardo, Laurie, et al., "Placement of Endovascular Embolization Microcoils to Localize the Site of Breast Lesions Removed at Stereotactic Core Biopsy", Radiology, Jan. 1998, pp. 275-278, vol. 206—No. 1.

H. J. Gent, M.D., et al., Stereotaxic Needle Localization and Cytological Diagnosis of Occult Breast Lesions, Annals of Surgery, Nov. 1986, pp. 580-584, vol. 204—No. 5.

Meuris, Bart, "Calcification of Aortic Wall Tissue in Prosthetic Heart Valves: Initiation, Influencing Factors and Strategies Towards Prevention", Thesis, 2007, pp. 21-36, Leuven University Press; Leuven, Belgium.

Shah, et al. (Polyethylene Glycol as a Binder for Tablets, vol. 66, No. 11, Nov. 1977, Journal of Pharmaceutical Sciences).

Armstong, J.S., et al., "Differential marking of Excision Planes in Screened Breast lesions By Organically Coloured Gelatins", Journal of Clinical Pathology, Jul. 1990, No. 43 (7) pp. 604-607, XP000971447 abstract; tables 1,2.

Fucci, V., et al., "Large Bowel Transit Times Using Radioopaque Markers in Normal Cats", J. of Am. Animal Hospital Assn., Nov.-Dec. 1995 31 (6) 473-477.

Schindlbeck, N.E., et al., "Measurement of Colon Transit Time", J. of Gastroenterology, No. 28, pp. 399-404, 1990.

Shiga, et al., Preparation of Poly(D, L-lactide) and Copoly(lactide-glycolide) Microspheres of Uniform Size, J. Pharm. Pharmacol. 1996 48:891-895.

Eiselt, P. et al, "Development of Technologies Aiding Large-Tissue Engineering", Biotechnol. Prog., vol. 14, No. 1, pp. 134-140, 1998.

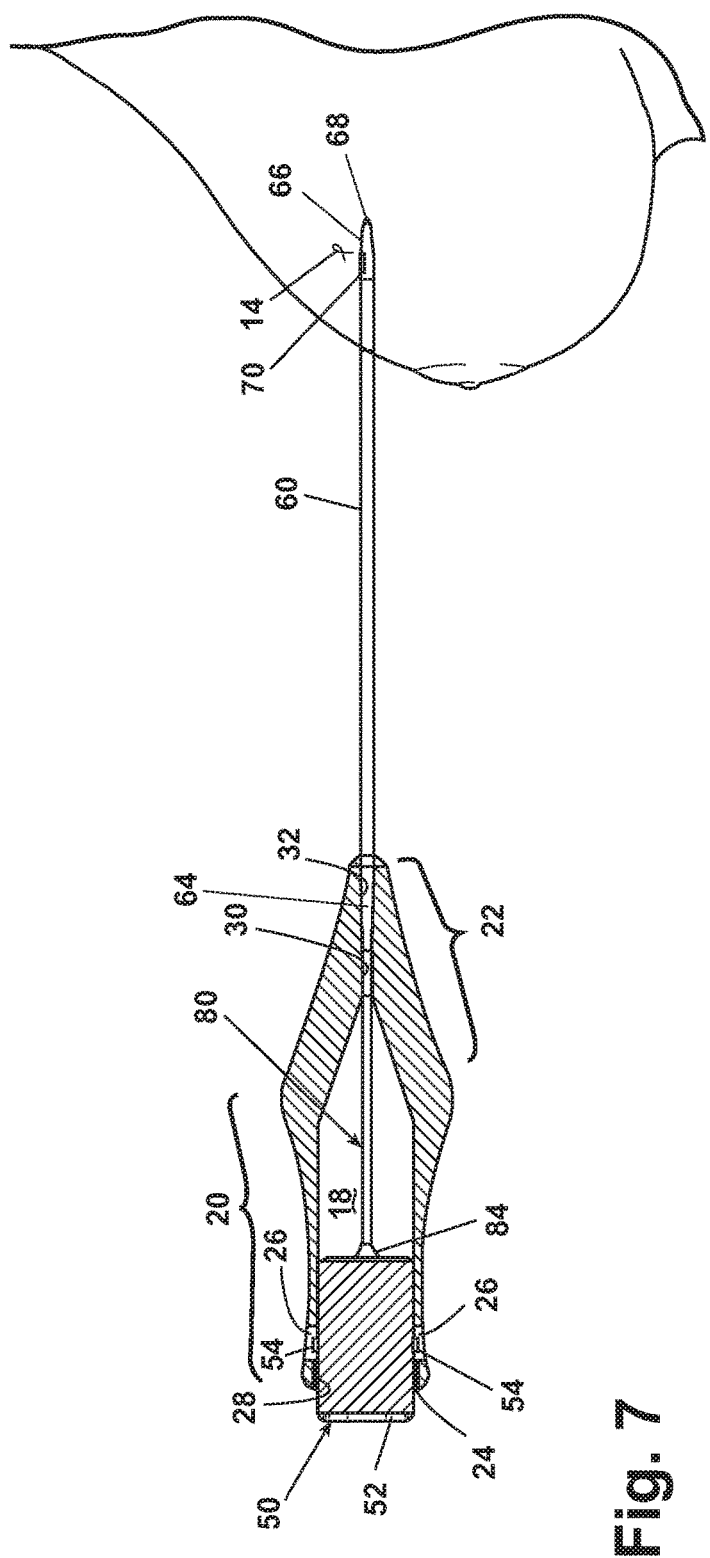
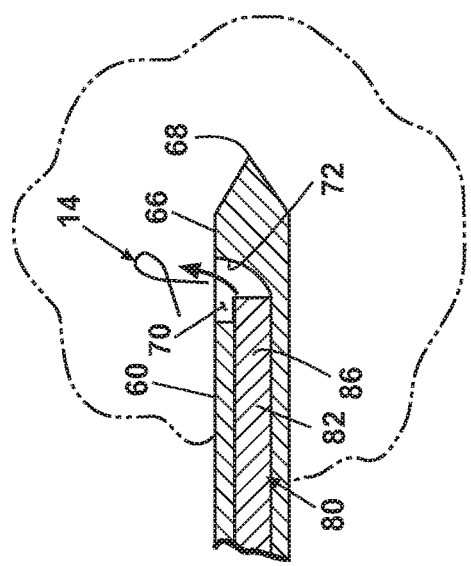
Fig. 7
Fig. 8

## SELF-CONTAINED, SELF-PIERCING, SIDE-EXPELLING MARKING APPARATUS

CROSS-REFERENCE TO RELATED APPLICATIONS

This application is a continuation of U.S. application Ser. No. 15/381,717 filed Dec. 16, 2016, now U.S. Pat. No. 9,848,956, which is a divisional of U.S. application Ser. No. 15/078,847 filed Mar. 23, 2016, now abandoned, which is a continuation of U.S. application Ser. No. 12/850,844 filed Aug. 5, 2010, now abandoned, which is a continuation of U.S. application Ser. No. 11/275,918 filed Feb. 3, 2006, now U.S. Pat. No. 7,819,820, which is a continuation of U.S. application Ser. No. 10/710,587 filed Jul. 22, 2004, now abandoned, and is a continuation-in-part of U.S. application Ser. No. 10/707,044 filed Nov. 17, 2003, now U.S. Pat. No. 7,424,320, issued Sep. 9, 2008, which claims the benefit of U.S. Provisional Application Ser. No. 60/427,048 filed Nov. 18, 2002, all of which are incorporated herein by reference in their entirety.

BACKGROUND OF THE INVENTION

Field of the Invention

This invention relates generally to an apparatus for the percutaneous positioning of an imaging marker for identifying the location of a lesion in a biopsy procedure. More particularly, the invention relates to a self-contained marking apparatus that expels the imaging marker through the side of the marking device.

Description of the Related Art

Tissue biopsies are commonly performed on many areas and organs of the body where it is desirable to ascertain whether or not the biopsied tissue is cancerous. Often, a lesion or other tissue to be biopsied is identified through use of an imaging technique such as a computerized axial tomography (CAT) scan, ultrasonography, magnetic resonance imaging, and mammography.

One problem commonly encountered, especially in breast biopsies, is that the lesion is so small that the biopsy reduces its size to the extent that it is no longer visible by the imaging method employed. In such circumstances, it is desirable to place an imaging marker at the site of the biopsy to enable the medical practitioner subsequently to locate the lesion quickly and accurately in the event complete removal of the affected tissue is indicated. This problem is currently met by placing an imaging marker at the biopsy area by means of a cannula or similar device housing the marker.

There are currently two primary types of marking devices. One of the primary types is referred to as vacuum assisted biopsy devices (VAB's). The VAB devices are many times integrated with a mammography imaging system. They include a large diameter cannula, approximately 9 to 12 gage, or probe that is inserted into the breast tissue. Instruments, such as a biopsy device and a marking device, are introduced into the breast tissue through the large diameter cannula to take biopsy samples or mark a biopsy location.

The other primary type is self-contained marking devices comprising a small diameter, approximately 14 to 17 gage, open-end cannula and a stylet slidably received within the cannula. A marker is located in the cannula and expelled out the open-end upon the advancing of the stylet relative to the cannula.

One disadvantage of the VAB system is the biopsy and marking tools are integrated with the mammography imaging system. The capital investment of this type of system is substantial. Also, the biopsy and marking tools are typically designed to work only with the large diameter probe, which tends to lock the hospital or medical professional into the same source for the imaging system and the biopsy and marking tools. The VAB systems are also intended for the same components to be reused, which requires sterilization after each step. The various components are also typically flexible to help insert them through the probe. The VAB systems also have a relatively large diameter probe, which, all things being equal, the larger the diameter, the greater trauma to the surrounding tissue and the greater the pain or discomfort for the patient.

The self-contained marking devices address these disadvantages of the VAB systems. Since the self-contained marking device is not integrally incorporated with a particular imaging system, the self-contained marking devices can be used with any suitable imaging system and are not limited to just mammography. This permits the hospital or medical professional to mix and match the available imaging systems and self-contained marking devices to obtain the desired performance and cost-effectiveness.

The self-contained marking devices are typically disposable, which negates the need to sterilize them after each use. They also have a much smaller diameter, resulting in much less trauma to the surrounding tissue and pain to the patient.

A disadvantage of the self-contained systems is that the cannula has an open tip through which the marker is expelled. The open tip is generally closed by the marker residing in the cannula. However, the marker does not completely close off the open tip and it is possible for tissue to enter the open end of the cannula during the positioning of the marking device. The presence of tissue inside the open end of the cannula can interfere or make more difficult the expelling of the marker from the cannula.

The possibility for tissue being present in the open end of the cannula is, to some extent, related to the distance that the cannula is inserted through the tissue to the marking site. Thus, the manner in which the marking device is located at the biopsy site can impact the presence of tissue in the open end of the cannula. For example, the self-contained systems are sometimes used in combination with a positioning cannula that is inserted into the tissue mass with a stylet closing the end of the positioning cannula. In such a configuration, the stylet is removed once the positioning cannula is properly located relative to the biopsy site. Both the biopsy device and the marking device can be inserted and withdrawn through the positioning cannula. The use of the positioning cannula reduces the distance that the open end of the marking device cannula must travel through the tissue.

Alternatively, the marking device can be inserted without the positioning cannula. This is most common when it is desirable to place a marker without taking a biopsy. Under such circumstances, it is more likely that tissue will be received within the open end of the cannula. Therefore, it is more likely that the tissue will interfere with the expelling of the marker.

Therefore, it is desirable to have a self-contained marking device that can be used with or without a positioning cannula and which does not receive tissue within the open end of the cannula that might interfere with the expelling of the marker.

SUMMARY OF THE INVENTION

The invention relates to a marking apparatus for the percutaneous placement of an imaging marker at a predetermined location in a tissue mass to facilitate subsequent determination of the predetermined location. The marking apparatus comprises a handle, cannula, and plunger. The handle is to be grasped by a user to aid in the placement of the marker.

The cannula comprises a peripheral wall forming a lumen, with a proximal end carried by the handle, and a distal end terminating in a self-piercing tip. A lateral opening is formed in the peripheral wall and is open to the lumen.

A plunger having a distal end is slidably received within the lumen for movement between a ready position, where the distal end is spaced inwardly from the self-piercing tip to form a marker recess in communication with the lateral opening and sized to receive an imaging marker, and an expelled position, where the distal end is advanced a sufficient distance into the marker recess to expel a marker contained therein through the lateral opening.

One or more imaging markers can be positioned within the marker recess.

The handle, cannula, plunger are operably coupled such that they form a self-contained marking apparatus that can be easily and conveniently handled by a user to effect operation of the marking apparatus from the ready position to an expelled position.

The cannula is preferably sufficiently rigid and a distal end of the cannula is pointed to form the self-piercing tip. The cannula is 13 gage or less.

A ramp can be provided on at least one of the plunger and cannula to aid in expelling an imaging marker. The ramp can be located in the lumen adjacent the lateral opening. The distal end of the plunger can be flexible to be deflected toward the lateral opening by the ramp when the plunger is moved to the expelled position. The ramp can also be located on the distal end of the plunger.

The invention, in one form thereof, is directed to a marking apparatus for the percutaneous placement of an imaging marker in a tissue mass. The marking apparatus includes a handle to be grasped by a user, a rigid cannula and a stylet. The rigid cannula has a peripheral wall forming a lumen that carries the imaging marker, a proximal end coupled to the handle, a lateral opening in the peripheral wall that is open to the lumen, and a closed-off distal portion having a ramp adjacent the lumen. The closed-off distal portion extends distally from the ramp to terminate at a tissue piercing pointed tip. The ramp of the rigid cannula is curved to transition from the peripheral wall of the rigid cannula to the lateral opening of the rigid cannula. A stylet has a distal end, with at least the distal end of the stylet being flexible. The stylet is slidably received within the lumen of the rigid cannula for movement in the lumen. The ramp of the rigid cannula is adapted to engage the distal end of the stylet as the stylet is advanced through the lumen of the rigid cannula to guide the distal end of the stylet to a position to substantially close off the lateral opening of the rigid cannula having the tissue piercing tip.

The invention, in another form thereof, is directed to a marking apparatus for the percutaneous placement of an imaging marker in a tissue mass. The marking apparatus includes a handle to be grasped by a user, a cannula, and a stylet. The cannula has a peripheral wall forming a lumen that carries the imaging marker, a proximal end coupled to the handle, a lateral opening in the peripheral wall that is open to the lumen, and a closed-off distal portion having a ramp adjacent the lumen. The closed-off distal portion extends distally from the ramp to terminate at a tissue piercing pointed tip. The stylet has a distal end with an angled surface. The stylet is disposed in the lumen and movable in the lumen between a ready position and an expelled position, such that when the stylet is advanced through the lumen to the expelled position the ramp deflects the distal end of the stylet toward the lateral opening such that at the expelled position the angled surface is flush with the peripheral wall of the cannula at the lateral opening of the cannula.

The invention, in another form thereof, is directed to a marking apparatus for the percutaneous placement of an imaging marker in a tissue mass. The marking apparatus includes a handle to be grasped by a user, a cannula, and a stylet. The cannula has a peripheral wall forming a lumen that carries the imaging marker, a proximal end carried by the handle, a closed-off distal portion terminating in a self-piercing tip, a ramp integrated with the closed-off distal portion, and a lateral opening in the peripheral wall. The lateral opening extends in a region between the proximal end and the closed-off distal portion of the cannula. The lateral opening has a proximal extent and a distal extent, the distal extent being closer to the self-piercing tip than the proximal extent. The stylet includes a distal end. The stylet is slidably received within the lumen for movement between a ready position, wherein the distal end of the stylet is spaced inwardly from the self-piercing tip to form a marker recess in communication with the lateral opening, and an expelled position, wherein the distal end of the stylet is advanced a sufficient distance into the marker recess to expel the imaging marker contained in the lumen through the lateral opening of the cannula. When the distal end of the stylet is at the expelled position the distal end of the stylet is deflected by the ramp to close off the lateral opening of the cannula between the proximal extent and the distal extent of the lateral opening.

The invention also relates to a method for percutaneously placing a marker at a predetermined location in a tissue mass using a self-piercing, side-ejecting, self-contained marking apparatus comprising a cannula defining a lumen and terminating in a self-piercing tip, with a lateral opening in communication with the lumen, and a plunger slidably received within the lumen for expelling a marker in the lumen through the lateral opening. The method comprises: inserting the cannula into the tissue mass by puncturing an exterior of the tissue mass with the self-piercing tip, and expelling the marker through the lateral opening by sliding the plunger within the lumen.

The inserting step can comprise locating the lateral opening near a predetermined location in the tissue mass where it is desired to be marked. Preferably, the lateral opening is located beneath the predetermined location.

The expelling step comprises expelling multiple markers into the tissue mass. At least one of the multiple markers can be expelled at a different location in the tissue mass than another of the multiple markers.

BRIEF DESCRIPTION OF THE DRAWINGS

In the drawings:

FIG. 7 is a sectional view of the marking device inserted into a tissue mass such that the cannula side opening is adjacent an area to be marked, with the stylet shown in a expelled position and the marker expelled through the side opening into the surrounding tissue mass.

FIG. 8 is an enlarged sectional view of the cannula tip of FIG. 7.

DETAILED DESCRIPTION

Figure 1:
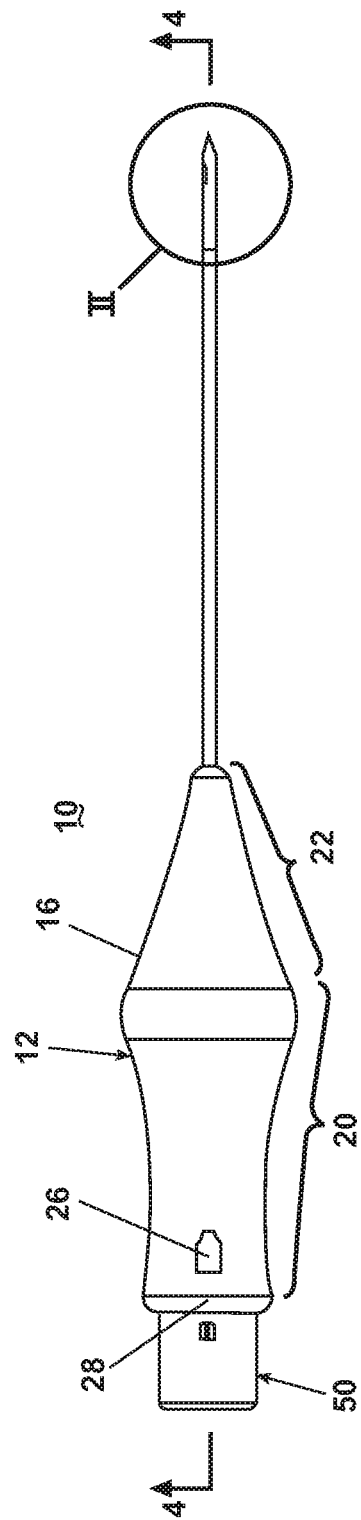
FIG. 1 is a plan view of a self-contained, self-piercing, and side-expelling marking apparatus comprising an actuator, a cannula with a side opening, and a stylet for laterally expelling a marker through the side opening in accordance with the invention.
Figure 3:
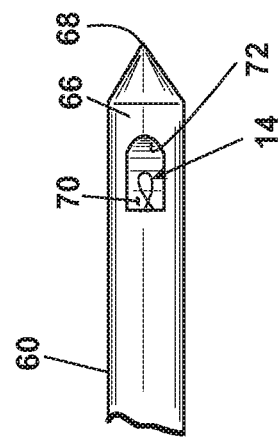
FIG. 3. is an enlarged top view of the cannula tip of FIG. 2.
Figure 2:
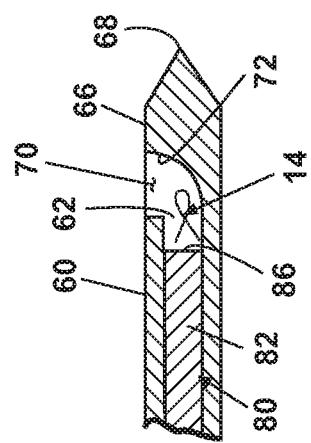
FIG. 2 is an enlarged sectional view of the area II of FIG. 1, illustrating the relationship between the cannula, stylet and marker prior to the expelling of the marker.
Figure 4:
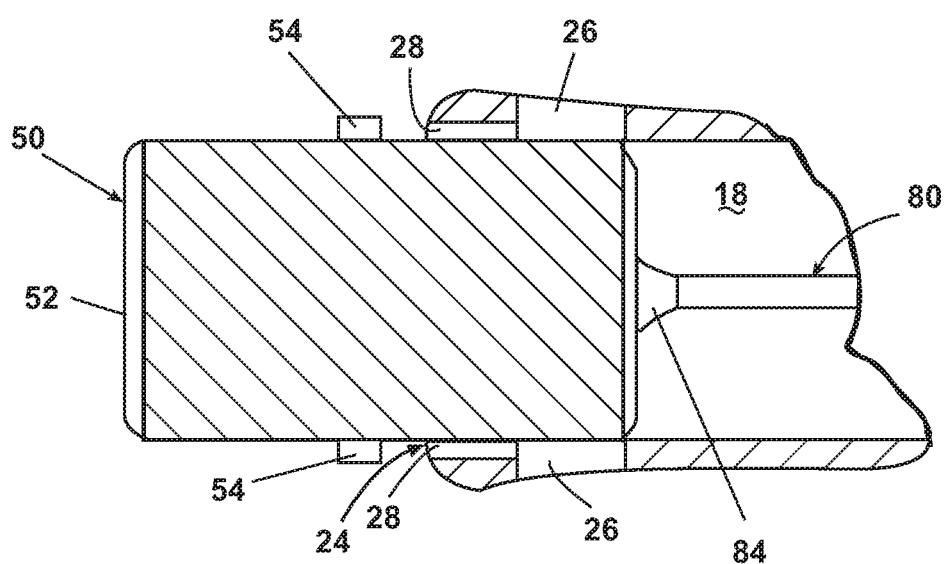
FIG. 4. is an enlarged sectional view of a portion of the actuator.

FIGS. 1-4 illustrate a self-contained, self-penetrating, side-expelling marking apparatus 10 according to the invention, which is capable of the percutaneous placement of a imaging marker at a desired location, such as at a tissue biopsy site or a lesion site in a breast. The marking apparatus 10 comprises an introducer 12 and an imaging marker 14 (FIG. 2) contained within the introducer 12. The introducer 12 includes an actuator 16 having a hollow interior 18. The actuator 16 comprises a grip portion 20 from which extends a tapered nose portion 22. The grip portion 20 defines a rear opening 24 that provides access to the hollow interior 18. A pair of detents 26 are formed in the grip portion 20 near the rear opening 24. Channels 28 are formed on the interior surface of the grip portion 20 and extend from the rear opening 24 to the detents 26.

Figure 5:
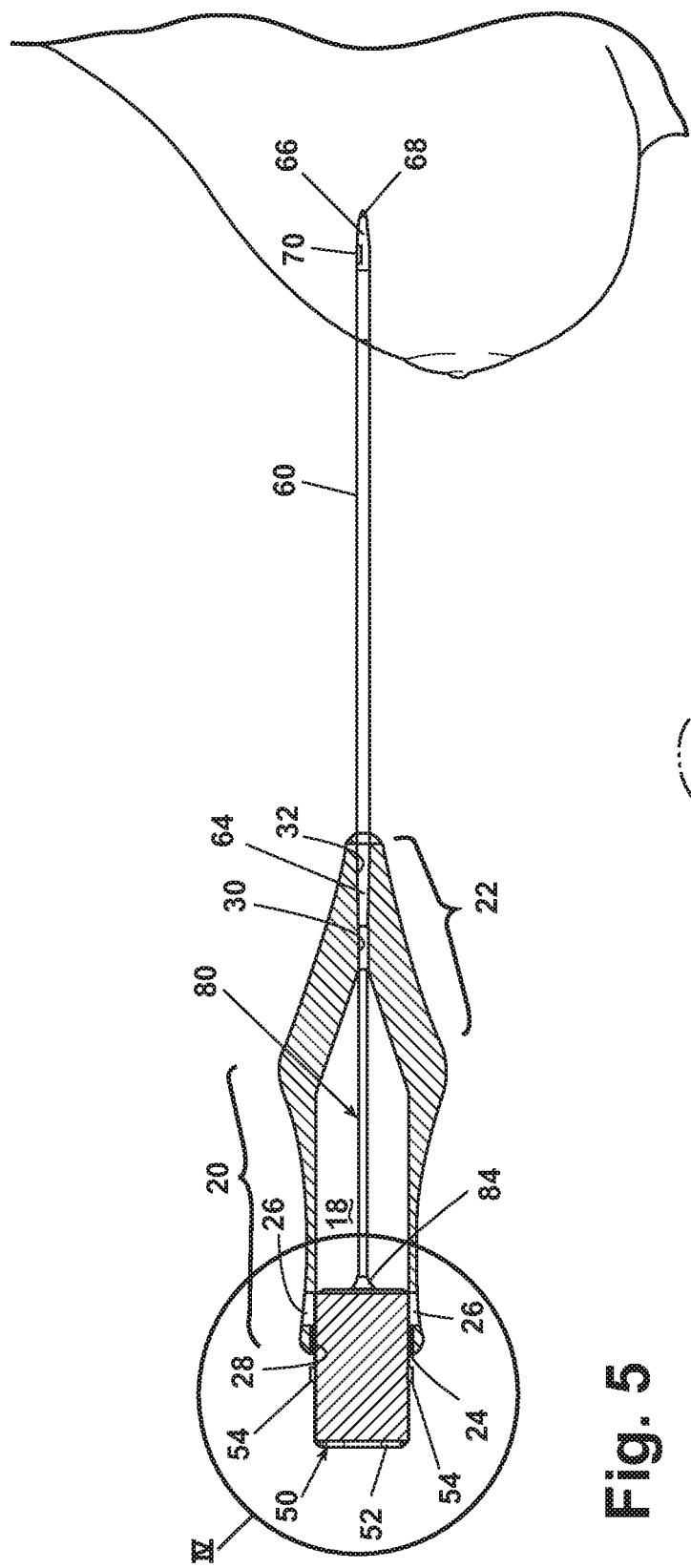
FIG. 5 is a sectional view of the marking device inserted into a tissue mass such that the cannula side opening is adjacent an area to be marked, with the stylet shown in a ready position and the marker still retained within the cannula lumen.

The nose portion 22 comprises a guide passage 30 extending from the tip of the nose portion 22 to the hollow interior 18 of the actuator 16. The guide passage 30 decreases in diameter inwardly from the tip of the nose portion to form a cannula seat 32 (FIG. 5).

A plunger 50 comprises a cylindrical body 52 from which extend a pair of catches 54 at diametrically opposed positions. The cylindrical body 52 is sized so that it is slidably received within the rear opening 24 of the actuator 16 where it is so oriented with respect to the actuator such that the catches 54 are aligned with the guide channels 28. The plunger is free to reciprocate within the grip portion 20 of the actuator 16.

A cannula 60 is mounted to the introducer 12. The cannula 60 defines a hollow interior in the form of a lumen 62 and comprises a proximal end 64 and a distal end 66. The proximal end 64 (FIG. 5) is mounted within the cannula seat 32 to secure the cannula 60 to the introducer 12. The distal end 66 terminates in a closed-off tip 68 to provide the marking apparatus with self-piercing functionality. The closed-off tip 68 is illustrated as being pointed, but other suitable shapes are possible.

The cannula 60 is preferably 13 gage or less in size. The cannula 60 is also preferably rigid. That is, the cannula does not substantially flex. The rigidity of the cannula aids in inserting the cannula into a tissue mass, without the aid of a guide needle or guide cannula.

A side opening 70 is formed in the cannula 60 and extends entirely through the cannula such that the lumen 62 is in communication with the exterior of the cannula 60 through the side opening 70. The side opening is preferably located behind the closed-off tip 68.

A ramp 72 is provided on the interior of the cannula 60. The ramp 72 is illustrated as being integrally formed with the closed-off tip 68. Such a configuration can result in a solid distal end 66 as illustrated. However, the distal end can be hollow and the ramp 72 can be formed by separately from the distal end 66.

The ramp 72 extends diametrically across the lumen 62 and terminates at the side opening 70. With this configuration, the ramp 72 aids in directing an imaging marker 14 stored in the lumen through the side opening 70 and beyond the exterior of the cannula.

A stylet 80 comprising a shaft 82 and a base 84 is received within the hollow interior 18 of the actuator 16 in a manner such that the shaft 82 extends through the guide passage 30 and into the cannula interior 62 and the stylet base 84 lies within the hollow interior 18 and is mounted to the plunger 50. Thus, the reciprocation of the plunger 50 relative to the grip portion 20 results in a reciprocation of the stylet 80 within the cannula 60.

The stylet 80 terminates in a distal end 86, which, when the marking apparatus is in the ready position, is spaced from the distal end 66 of the cannula 60 to form a marker recess therebetween. As illustrated, a single marker 14 is stored within the marker recess. It is within the scope of the invention for multiple markers to be received within the marker recess.

As is shown, the foregoing construction provides a marking apparatus that is preassembled as a self-contained unit and prepackaged, all under sterile conditions, thereby affording the practitioner substantially greater convenience and reliability, while eliminating the need for sterilizing the self-contained unit after use. Preferably, the self-contained unit is disposed of after it is used.

Figure 6:
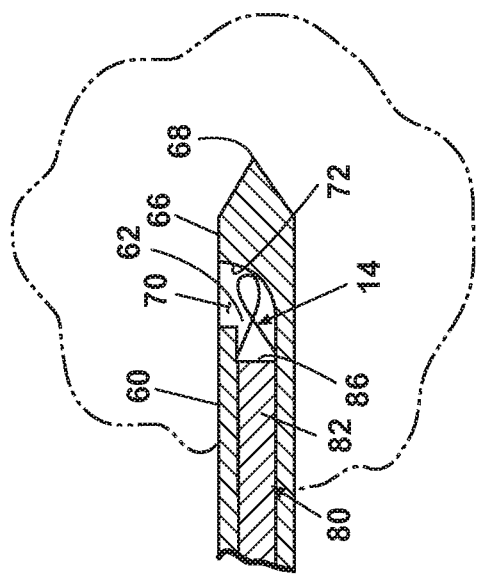
FIG. 6 is an enlarged sectional view of the cannula tip of FIG. 5.

Referring to FIGS. 5-8, in operation, the introducer 12 begins in the ready condition shown in FIGS. 5 and 6. In this condition, the distal end 86 of the stylet 80 is received within the cannula and spaced from the closed-off distal end 66 of the cannula to define a marker recess in which a marker 14 is stored. The plunger 50 is in a position relative to the grip portion 20 in which the catches are outside the grip portion; that is, they are not received within the detents 26. However, the plunger 50 is so oriented with respect to the grip portion that the catches 54 are aligned with the guide channels 28.

With the introducer in the ready condition, the cannula is positioned within the tissue mass such that the side opening 70 is at or near the location of a tissue mass where it is desired to place the marker. In the case of marking a biopsy site, the side opening is preferably placed adjacent the biopsy site.

To place the side opening adjacent the site to be marked, the medical professional grasps the grip portion 20 of the actuator and presses the closed-off tip 68 against the exterior of the tissue mass to puncture the tissue mass. The medical professional continues applying force to the grip portion 20 to drive the cannula 60 to the desired location within the tissue mass.

The closed tip 68 helps separate the tissue of the tissue mass to make it easier to insert the cannula within the tissue mass to the desired location. A starter incision can be made in the exterior of the tissue mass to reduce the initial force need to start the insertion.

The used of a side opening 70 instead of a tip opening found in the prior art self-contained devices helps prevent the accumulation of tissue within the lumen 62 upon the insertion of the cannula 60 into the tissue mass. The closed tip 68 also helps in that it separates the tissue to form a path through which the side opening passes. Since the side opening is parallel to the path, there is much less tendency for the insertion of the cannula to force tissue into the side opening as could occur in the prior-art front opening cannulae.

Typically, a suitable imaging system will be used by the medical professional to help guide the cannula to the desired location within the tissue mass. Examples of contemporary imaging systems include: stereotactic, x-ray, ultrasound, CAT scan, or MRI. The invention is not limited to any particular type of imaging system.

Once the cannula is positioned at the desired location, the plunger 50 is moved from a first or ready condition as illustrated in FIGS. 5 and 6 to a second or expelled condition as illustrated in FIGS. 7 and 8. As the plunger is moved, the stylet 80 is advanced into the marker recess to drive the marker 14 up the ramp 72. The continued advancement of the stylet 80 ultimately drives the marker 14 through the side opening 70 and into the adjacent tissue.

Once the stylet is in the expelled position, the cannula can be withdrawn to leave the marker in the tissue. To withdraw the cannula, the medical professional pulls on the actuator to withdraw the cannula from the tissue mass. After use, the marking apparatus is disposed of, negating the need for sterilization.

As illustrated, the rigid cannula in combination with the closed-off tip 68 provides an ideal structure for inserting the device directly into the tissue without the need for a guide needle or cannula. This is advantageous in that it reduces the size of the opening formed in the tissue and thereby reducing the trauma to the patient. The closed-off tip is used to puncture the exterior of the tissue mass. While the marking apparatus of the invention can be used with a guide needle or cannula, there is no need to do so because of the self-piercing nature of the invention.

Figure 9:
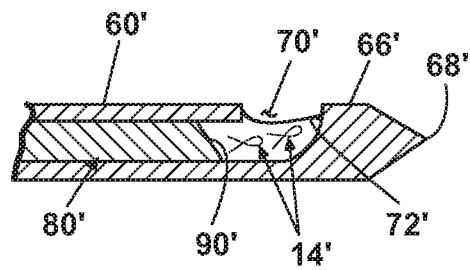
FIG. 9 is a sectional view of an alternative design for the cannula and stylet according to the invention, with the stylet having a flexible tip and shown in the ready position.
Figure 10:
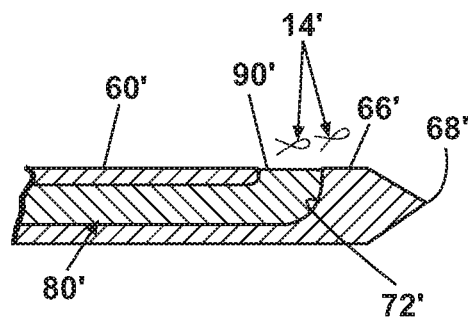
FIG. 10 is a sectional view of the cannula and stylet of FIG. 9 with the stylet shown in the expelled position.

FIGS. 9 and 10 illustrate an alternative design for the stylet in the ready and expelled conditions, respectively. The alternative stylet 80' is essentially identical to the stylet 80, except that the distal end 66' is made from a resilient material and has an angled surface 90'. The resilient material permits the distal end 66' to deflect when contacting the ramp 72', such that the distal end 66' generally follows the shape of the ramp 72'. The angle of the angled surface 90' is preferably selected such that the angled surface substantially closes off the side opening 70' when the stylet is in the expelled condition, which will ensure that the marker is completely expelled through the side opening 70'. It will also ensure that no portion of the marker 14 will be pulled back into the side opening 70' due to the vacuum forces created upon the withdrawal of the cannula. The angled surface 90' functions like the ramp 72 in that it helps to deflect the marker 14 through the side opening.

Figure 11:
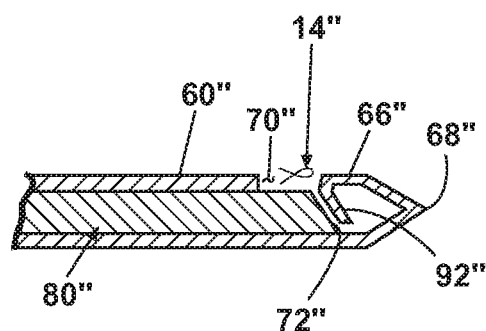
FIG. 11 is a sectional view of a second alternative design for the cannula and stylet according to the invention, with the stylet having a ramped tip and shown in the expelled position.

FIG. 11 illustrates another alternative design for the stylet and cannula. In this alternative design, the distal end 66" of the stylet 80" includes a ramp 72". A resilient end wall 92" is used instead of the ramp 72 of the cannula. The space between the ramp 72" and the resilient end wall 92" defines the marker recess in which multiple markers 14" are stored. The advancement of the stylet from the ready condition to the expelled condition drives the markers up the ramp 72". When contacted by the ramp 72", the resilient end wall 92" deflects to permit the ramp 72" to slide beneath and into the distal end closed tip 68" of the cannula.

In all of the embodiments, multiple markers can be located within the cannula and expelled at the same or different locations within the tissue mass.

While the invention has been specifically described in connection with certain specific embodiments thereof, it is to be understood that this is by way of illustration and not of limitation, and the scope of the appended claims should be construed as broadly as the prior art will permit.

We claim:

1. A method of operating a tissue marking apparatus, comprising:
   providing a tissue marking apparatus having a cannula, a stylet, and an imaging marker, the cannula having a peripheral wall forming a lumen and a lateral opening in the peripheral wall that is open to the lumen, and having a resilient end wall extending downwardly from the peripheral wall at a distal extent of the lateral opening, the stylet being slidably received within the lumen of the cannula for movement in the lumen;
   moving the stylet in a distal direction to expel the imaging marker from the lateral opening; and
   continue moving the stylet in the distal direction to deflect the resilient end wall of the cannula such that a distal end of the stylet passes beneath the resilient end wall to substantially close off the lateral opening of the cannula.

2. The method of claim 1, wherein only the stylet and the resilient end wall close off the lateral opening when the stylet is in an extended position.

3. The method of claim 1, comprising:
   positioning the stylet in a ready position wherein a distal end of the stylet is positioned in the lumen proximal to an extended position to form a marker recess to carry the imaging marker; and
   the act of moving moves the stylet to the extended position to substantially close off the lateral opening of the cannula only after the imaging marker is expelled.

4. The method of claim 3, comprising positioning multiple imaging markers within the marker recess.

5. The method of claim 1, comprising latching the stylet in an extended position.

6. A method of operating a tissue marking apparatus, comprising:
   providing a tissue marking apparatus having a handle, a cannula, a stylet, and an imaging marker, the cannula having a peripheral wall forming a lumen that carries the imaging marker, a proximal end coupled to the handle, a lateral opening in the peripheral wall that is open to the lumen, a closed-off distal portion having a distal void and a pointed tip, wherein the distal void is distal to the lateral opening and is proximal to the pointed tip, and a resilient end wall proximal to the distal void, the stylet having a distal end with an angled surface, the stylet being disposed in the lumen and movable in the lumen;
   advancing the stylet through the lumen to expel the imaging marker out of the lumen through the lateral opening of the cannula; and
   further advancing the stylet through the lumen to deflect the resilient end wall and to pass beneath the resilient end wall and into the distal void.

7. The method of claim 6, wherein the resilient end wall cantilevers from the peripheral wall of the cannula to separate the distal void from the lateral opening.

8. The method of claim 6, wherein the stylet closes off the lateral opening after the imaging marker is expelled.

9. The method of claim 8, wherein after the imaging marker is expelled, further comprising latching the stylet.

10. A method of operating a tissue marking apparatus, comprising:

providing a tissue marking apparatus having a cannula, a stylet, and an imaging marker, the cannula having a lumen, a lateral opening in a peripheral wall, a cantilever end wall extending into the lumen from the peripheral wall, and a closed-off distal portion, the cantilever end wall having a distal free end that is suspended in the lumen above the peripheral wall;

moving a stylet within the lumen to expel an imaging marker from the lateral opening of the cannula; and continuing movement of the stylet in the lumen of the cannula to deflect the cantilever end wall and to pass the stylet beneath the cantilever end wall and into the closed-off distal portion.

11. The method of claim 10, wherein the stylet has an angled end surface to engage the cantilever end wall.

12. The method of claim 10, comprising latching the stylet in an extended position.

* * * * *